United States Patent [19]

Leppard et al.

[11] Patent Number: 5,399,782
[45] Date of Patent: Mar. 21, 1995

[54] BENZOYL-SUBSTITUTED PHOSPHABICYCLOALKANES AND PHOSPHABICYCLOALKANESULFIDES AS PHOTOINITIATORS

[75] Inventors: David G. Leppard, Marly; Ljubomir Misev, Allschwil; Gebhard Hug, Fribourg, all of Switzerland

[73] Assignee: Ciba-Geigy Corporation, Ardsley, N.Y.

[21] Appl. No.: 27,626

[22] Filed: Mar. 8, 1993

[30] Foreign Application Priority Data

Mar. 11, 1992 [CH] Switzerland ............... 786/92

[51] Int. Cl.⁶ ............................................... C07F 9/02
[52] U.S. Cl. ............................ 568/12; 430/269; 522/55; 522/56; 522/64
[58] Field of Search .................. 568/12; 430/269; 522/55, 56, 64

[56] References Cited

U.S. PATENT DOCUMENTS

| | | | |
|---|---|---|---|
| 3,673,231 | 6/1972 | Morris | 568/12 |
| 4,298,738 | 11/1981 | Lechtken et al. | 546/22 |
| 4,324,744 | 4/1982 | Lechtken et al. | 260/932 |
| 4,522,693 | 6/1985 | Henne et al. | 204/159.15 |
| 5,218,009 | 6/1993 | Rutsch | 522/16 |

FOREIGN PATENT DOCUMENTS 0047902 3/1982 European Pat. Off. .
0040721 5/1990 European Pat. Off. .
0413657 2/1991 European Pat. Off. .

OTHER PUBLICATIONS

C.A. 96:105234q (1982).

*Primary Examiner*—Marion E. McCamish
*Assistant Examiner*—Mark A. Chapman
*Attorney, Agent, or Firm*—Luther A. R. Hall

[57] ABSTRACT

Compounds of formula I

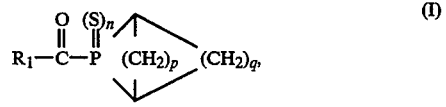

wherein n is 0 or 1,
p is a number from 1 to 8,
q is 2 or 3, and
$R_1$ is unsubstituted phenyl or phenyl which is substituted by one to three halogen, $C_1$–$C_8$alkyl, $C_1$–$C_8$alkoxy, $C_2$–$C_8$alkoxyalkyl or/and $C_1$–$C_4$alkylthio, are suitable for use as initiators for photopolymerising compounds containing ethylenically unsaturated double bonds.

7 Claims, No Drawings

BENZOYL-SUBSTITUTED PHOSPHABICYCLOALKANES AND PHOSPHABICYCLOALKANESULFIDES AS PHOTOINITIATORS

The present invention relates to benzoyl-substituted phosphabicycloalkanes and phosphabicyclosulfides, to their use as initiators for photopolymerising ethylenically unsaturated compounds, and to compositions comprising benzoyl-substituted phosphabicycloalkanes and phosphabicyclosulfides.

Monoacylphosphine oxides and theft use as photoinitiators are known to those skilled in the art from, inter alia, U.S. Pat. No. 4,298,738 and EP-A-40 721 as well as from a host of other publications. The preparation of acylphosphine sulfides and their use as photoinitiators is disclosed in U.S. Pat. No. 4 522 693. Benzoyl-substituted phosphabicycloalkane oxides having photoinitiating properties are disclosed for the first time in EP-A-413 657.

There is still a need in the an for effective photoinitiators.

Surprisingly, it has now been found that benzoyl-substituted phosphabicycloalkanes and phosphabicyclosulfides have very good photocuring properties.

Specifically, the invention relates to compounds of formula I $$R_1-\overset{O}{\underset{\|}{C}}-\overset{(S)_n}{\underset{\|}{P}}\underset{(CH_2)_p}{\overset{}{\diagup}}\underset{(CH_2)_q}{\overset{}{\diagdown}} \quad (I)$$

wherein n is 0 or 1;
p is a number from 1 to 8,
q is 2 or 3, and
$R_1$ is unsubstituted phenyl or phenyl which is substituted by one to three halogen, $C_1-C_8$alkyl, $C_1-C_8$alkoxy, $C_2-C_8$alkoxyalkyl or/and $C_1-C_4$alkylthio.

Substituted phenyl carries one or more than one substituent, preferably one to three, typically one or two and, most preferably, two or three substituents.

Halogen-substituted phenyl is substituted by chloro, bromo, fluoro or iodo, preferably by chloro, and is typically chlorophenyl, 2,4- or 2,6-dichlorophenyl, 2,4,6-trichlorophenyl, 2,4- or 2,6-dibromophenyl, 2,4,6-tribromophenyl, 2,4- or 2,6-difluorophenyl, and 2,4,6-trifluorophenyl. Halogen-substituted phenyl is preferably chlorophenyl.

$C_1-C_8$Alkyl substituents at the phenyl ring are branched or unbranched and are typically methyl, ethyl, propyl, isopropyl, n-butyl, sec-butyl, tert-butyl, pentyl, hexyl, heptyl or octyl. Methyl is preferred. Corresponding groups are typically tolyl, mesityl, xylyl, ethylphenyl or tert-butylphenyl. Mesityl is prefererd.

$C_1-C_8$Alkoxy-substituted phenyl is typically methoxyphenyl, dimethoxyphenyl, methhoxyethoxyphenyl, ethoxyphenyl, propoxyphenyl, methoxyisopropoxyphenyl, butoxyphenyl, dibutoxyphenyl or hexoxyphenyl. 2,6-Dimethoxyphenyl is preferred.

$C_2-C_8$Alkoxyalkyl-substituted phenyl is typically methoxymethylphenyl, methoxyethylphenyl, ethoxymethylphenyl, dimethoxymethylphenyl, dimethoxyethylphenyl, diethoxymethylphenyl, methoxyethylphenyl or ethoxyethylphenyl.

$C_1-C_4$Alkylthio-substituted phenyl is typically methylthiophenyl, ethylthiophenyl, propylthiophenyl, isopropylthiophenyl, butylthiophenyl or tert-butylthiophenyl.

Substituted phenyl may also carry several different substituents from among those mentioned above and is then typically 2,4-dibutoxy-6-methylphenyl, 2,4-dimethoxy-6-methylphenyl, 2,6-dimethoxy-4-methylphenyl, 2,4-diethoxy-6-methylphenyl, 2,4-diisopropoxy-6-methylphenyl.

Preferred compounds of formula I are those wherein $R_1$ is a radical of the formula II $$\underset{R_5}{\overset{R_4}{\diagdown}}\underset{}{\overset{R_2}{\diagup}}\underset{R_3}{\overset{}{\diagdown}} \quad (II)$$

wherein
$R_2$ and $R_3$ are each independently of the other halogen, preferably Cl, $C_1-C_4$alkyl or $C_1-C_4$alkoxy, and
$R_4$ and $R_5$ are each independently of the other halogen, preferably Cl, $C_1-C_4$alkyl or $C_1-C_4$alkoxy, or hydrogen.

Further interesting compounds of formula I are those wherein $R_4$ is $C_1-C_4$alkyl, $C_1-C_4$alkoxy or hydrogen and $R_5$ is hydrogen.

Particularly preferred compounds of formula I are those wherein $R_2$ and $R_3$ are each independently of the other $C_1-C_4$alkyl, preferably methyl, or $C_1-C_4$alkoxy, preferably methoxy, $R_4$ is hydrogen or $C_1-C_4$alkyl, preferably methyl, and $R_5$ is hydrogen.

Interesting compounds of formula I are those wherein $R_4$ is in the para-position of the phenyl ring.

Also preferred are compounds of formula I, wherein p is 1 to 4, preferably 3 and 4.

Compounds of formula I, wherein n is 1, are especially preferred.

Representative examples of compounds of formula I are: 9-(2,6-dimethoxybenzoyl)-9-phosphabicyclo[4.2.1]nonane 9-(2,6-dimethoxybenzoyl)-9-phosphabicyclo[3.3.1]nonane 9-(2,4,6-trimethylbenzoyl)-9-phosphabicyclo[4.2.1]nonane 9-(2,4,6-trimethylbenzoyl)-9-phosphabicyclo[3.3.1]nonane 9-(2,6-dichlorobenzoyl)-9-phosphabicyclo[4.2.1]nonane 9-(2,6-dichlorobenzoyl)-9-phosphabicyclo[3.3.1]nonane 9-(2,4-dibutoxy-6-methylbenzoyl)-9-phosphabicyclo[4.2.1]nonane 9-(2,4-dibutoxy-6-methylbenzoyl)-9-phosphabicyclo[3.3.1]nonane 9-(2,4-dimethoxy-6-methylbenzoyl)-9-phosphabicyclo[4.2.1]nonane 9-(2,4-dimethoxy-6-methylbenzoyl)-9-phosphabicyclo[3.3.1]nonane 9-(2,6-dimethoxybenzoyl)-7-phosphabicyclo[2.2.1]heptane 7-(2,4,6-trimethylbenzoyl)-7-phosphabicyclo[2.2.1]heptane 7-(2,6-dichlorobenzoyl)-7-phosphabicyclo[2.2.1]heptane 7-(2,4-dibutoxy-6-methylbenzoyl)-7-phosphabicyclo[2.2.1]heptane 7-(2,4-dimethoxy-6-methylbenzoyl)-7-phosphabicyclo[2.2.1]heptane 9-(2,6-dimethoxybenzoyl)-9-phosphabicyclo[4.2.1]nonane-9-sulfide 9-(2,6-dimethoxybenzoyl)-9-phosphabicyclo[3.3.1]nonane-9-sulfide 9-(2,4,6-trimethylbenzoyl)-9-phosphabicyclo[4.2.1]nonane-9-sulfide 9-(2,4,6-trimethylbenzoyl)-9-phosphabicyclo[3.3.1]nonane-9-sulfide 9-(2,6-dichlorobenzoyl)-9-phosphabicyclo[4.2.1]nonane-9-sulfide 9-(2,6-dichlorobenzoyl)-9-phosphabicyclo[3.3.1-

]nonane-9-sulfide 9-(2,4-dibutoxy-6-methylbenzoyl)-9-phosphabicyclo[4.2.1]nonane-9-sulfide 9-(2,4-dibutoxy-6-methylbenzoyl)-9-phosphabicyclo[3.3.1]nonane-9-sulfide 9-(2,4-dimethoxy-6-methylbenzoyl)-9-phosphabicyclo[4.2.1]nonane-9-sulfide 9-(2,4-dimethoxy-6-methylbenzoyl)-9-phosphabicyclo[3.3.1]nonane-9-sulfide 9-(2,6-dimethoxybenzoyl)-7-phosphabicyclo[2.2.1]heptane-7-sulfide 7-(2,4,6-trimethylbenzoyl)-7-phosphabicyclo[2.2.1]heptane-7-sulfide 7-(2,6-dichlorobenzoyl)-7-phosphabicyclo[2.2.1]heptane-7-sulfide 7-(2,4-dibutoxy-6-methylbenzoyl)-7-phosphabicyclo[2.2.1]heptane-7-sulfide 7-(2,4-dimethoxy-6-methylbenzoyl)-7-phosphabicyclo[2.2.1]heptane-7-sulfide The compounds of formula I (Ia: n=0, Ib: n=1) are prepared by reacting a bicyclic phosphane (II) with a carbonyl chloride (III) in the presence of a base. The sulfides (Ib) are obtained by subsequent reaction of compounds of formula (Ia) with an equimolar amount of elemental sulfur. The reactions are illustrated by the following scheme:

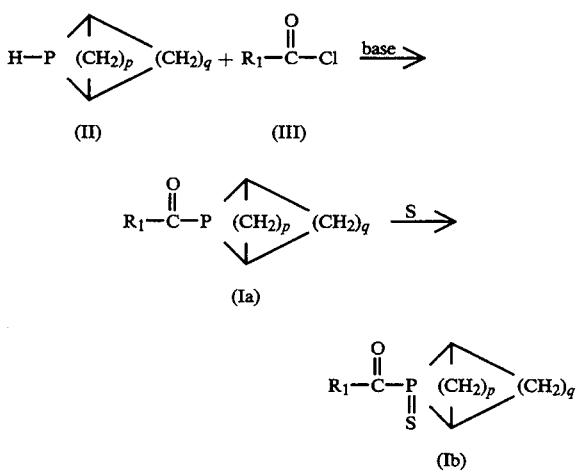

wherein $R_1$, p and q have the same meanings as defined in claim 1.

The reactions are preferably carded out in a suitable solvent. If components II and III are liquid, then it is also possible to carry out the first reaction step without a solvent. Particularly suitable solvents are hydrocarbons, typically alkanes and mixtures of alkanes, cyclohexane, benzene, toluene or xylene. Depending on the solvent and the educts used, the reaction will conveniently be carded out in the temperature range from 10 to 120° C., preferably from 20 to 80° C. If a solvent is used, it is removed by distillation upon completion of the reaction. The crude reaction products can be purified by distillation, crystallisation or chromatography.

The preparation of the sulfide is carded out in general accordance with the method described in U.S. Pat. No. 4,522,693. It is convenient to carry out the reaction in an inert gas atmosphere, typically nitrogen, argon or carbon dioxide, preferably nitrogen. After the reaction it may be necessary to separate the sulfide or the solution thereof from any remaining sulfur by filtration.

Suitable bases are alkali metal or alkaline earth metal carbonates, tertiary amines, alkali metals, lithium diisopropylamide, alkali metal alcoholates or alkali metal hydrides.

The preparation of the bicyclic phosphanes (II) is described, inter alia, in JP-A-80 123 790. Some of these compounds or mixtures thereof are also commercially available. The phosphanes may conveniently be obtained by addition of phosphine to a diene (IV):

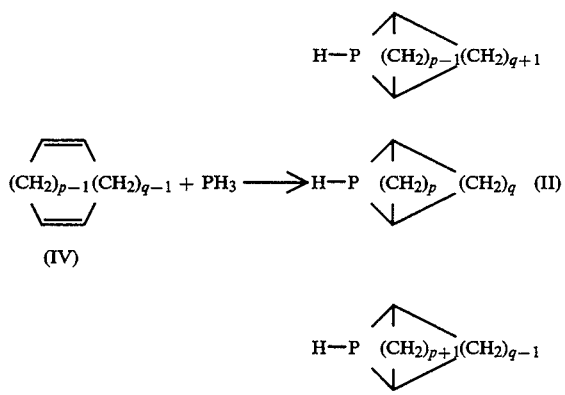

The ring size of the diene (IV) is p+q+2, where p and q are as defined in claim 1.

The starting dienes (IV) are known compounds, some of which are commercially available or are obtainable by methods similar to those used for preparing known compounds. The acid chlorides of formula (III) can also be prepared by known prior art methods.

In practice a start is often made from mixtures of isomers of the compounds of formula II, such mixtures being mainly obtained by addition of the phosphine to the compounds of formula (IV), as illustrated by the above reaction equation. In this case mixtures of the compounds of formula I will naturally also be obtained and likewise fall within the scope of claim 1. Formally, these mixtures are illustrated by formula I, wherein p and q are not whole numbers. If desired, said mixtures can also be separated by conventional methods, conveniently by chromatography. In practice, however, the mixtures themselves can be used as photoinitiators.

The compounds of formula I can be used in the practice of this invention as photoinitiators for the photopolymerisation of ethylenically unsaturated compounds or mixtures that contain such compounds.

The invention therefore also relates to photopolymerisable compositions comprising (a) at least one ethylenically unsaturated photopolymerisable compound, and (b) at least one compound of formula I as photoinitiator, which composition may additionally comprise at least one further photoinitiator and/or other additives.

The unsaturated compounds may contain one or more than one olefinic double bond. They may be low molecular (monomers) or high molecular (oligomers).

Exemplary monomers containing one double bond are alkyl or hydroxyalkyl acrylates or methacrylates, typically methyl, ethyl, butyl, 2-ethylhexyl or 2-hydroxyethyl acrylate, isobornyl acrylate, methyl- or ethyl methacrylate. Further examples are acrylonitrile, acrylamide, methacrylamide, N-substituted (meth)acrylamides, vinyl esters such as vinyl acetate, vinyl ethers such as isobutyl vinyl ether, styrene, alkyl styrenes and halostyrenes, N-vinylpyrrolidone, vinyl chloride or vinylidene chloride.

Exemplary monomers having several double bonds are ethylene glycol diacrylate, propylene glycol diacrylate, neopentyl glycol diacrylate, hexamethylene glycol diacrylate or hisphenol A diacrylate, 4,4'-bis(2-acryloyloxyethoxy)diphenylpropane, trimethylolpropane triacrylate, pentaerythritol triacrylate or tetraacrylate, pentaerythritol divinyl ether, vinyl acrylate, divinyl benzene, divinyl succinate, diallyl phthalate, triallyl phosphate, triallyl isocyanurate or tris(2-acryloylethyl)isocyanurate.

Typical examples of high molecular polyunsaturated compounds (oligomers) are acrylated epoxy resins, acrylated polyethers, acrylated polyurethanes or acrylated polyesters. Further examples of unsaturated oligomers are unsaturated polyester resins which are usually prepared from maleic acid, phthalic acid and one or more than one diol and which have molecular weights in the range from 500 to 3000. Such unsaturated diols can also be termed prepolymers.

Particularly suitable unsaturated compounds include esters of ethylenically unsaturated carboxylic acids and polyols or polyepoxides, and polymers containing ethylenically unsaturated groups in the chain or in side groups, including unsaturated polyesters, polyamides and polyurethanes and copolymers thereof, polybutadiene and butadiene copolymers, polyisoprene and isoprene copolymers, polymers and copolymers containing (meth)acrylic groups in side-chains, as well as mixtures of one or more than one such polymer.

Unsaturated carboxylic acids are typically acrylic acid, methacrylic acid, crotonic acid, itaconic acid, cinnamic acid, unsaturated fatty acids, such as linolenic acid or oleic acid. Acrylic acid and methacrylic acid are preferred.

Suitable polyols are aromatic polyols and, preferably, aliphatic and cycloaliphatic polyols. Illustrative examples of aromatic polyols are hydroquinone, 4,4'-dihydroxydiphenyl, 2,2-bis(4-hydroxyphenyl)propane, as well as novolaks and resols. Polyepoxides include those based on the cited polyols, preferably on the aromatic polyols and epichlorohydrin. Further suitable polyols are polymers and copolymers which contain hydroxyl groups in the polymer chain or in side groups, for example polyvinyl alcohol and copolymers thereof or polymethacrylic hydroxyalkyl esters or copolymers thereof. Other suitable polyols are oligoesters containing hydroxyl end groups.

Illustrative examples of aliphatic and cycloaliphatic polyols are alkylenediols containing preferably 2 to 12 carbon atoms, including ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably 200 to 1500, 1,3-cyclopentanediol, 1,2-, 1,3-or 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol and sorbitol.

The polyols may be esterified partially or completely with one or with different unsaturated carboxylic acids, in which case the free hydroxyl groups of the partial esters may be modified, for example etherified, or esterified with other carboxylic acids.

Illustrative examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentacrylate, dipentaerythritol hexacrylate, tripentaerythritol octacrylate, pentaerythritol dimethacrylate, pentaerythritol trimethacrylate, dipentaerythritol dimethacrylate, dipentaerythritol tetramethacrylate, dipentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentacrylate, sorbitol hexacrylate, oligoester acrylates and methacrylates, glycerol di- and-triacrylate, 1,4-cyclohexanediacrylate, bisacrylates and bismethacrylates of polyethylene glycol having molecular weights of 200 to 1500, or mixtures thereof.

Also suitable for use as component (a) are the amides of identical or different unsaturated carboxylic acids of aromatic, cycloaliphatic and aliphatic polyamines containing preferably 2 to 6, more particularly 2 to 4, amino groups. Exemplary of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, bis(13aminoethyl) ether, diethylenetriamine, triethylenetetramine, bis($\beta$-aminoethoxy)ethane or bis($\beta$-aminopropoxy)ethane. Other suitable polyamines are polymers and copolymers which may contain additional amino groups in the side-chain and oligoamides containing amino end groups. Exemplary of such unsaturated amides are: methylenebisacrylamide, 1,6-hexamethylenebisacrylamide, diethylenetriaminetrismethacrylamide, bis(methacrylamidopropoxy)ethane, $\beta$-methacrylamidoethylmethacrylate, N-[($\beta$hydroxyethoxy)ethyl]-acrylamide.

Suitable unsaturated polyesters and polyamides are derived typically from maleic acid and diols or diamines. Maleic acid can be partially replaced by other dicarboxylic acids. They can be used together with ethylenically unsaturated comonomers, as with styrene. The polyesters and polyamides can also be derived from dicarboxylic acids and ethylenically unsaturated diols or diamines, especially from those with long chains containing typically from 6 to 20 carbon atoms. Polyurethanes are typically those derived from saturated or unsaturated diisocyanates and unsaturated and saturated diols.

Polybutadiene and polyisoprene and copolymers thereof are known. Suitable comonomers include olefins such as ethylene, propene, butene, hexene, (meth)acrylates, acrylonitrile, styrene or vinyl chloride. Polymers containing (meth)acrylate groups in the side-chain are also known. They may typically be reaction products of epoxy resins based on novolak with (meth)acrylic acid, homo- or copolymers of polyvinyl alcohol or their hydroxyalkyl derivatives which are esterified with (meth)acrylic acid or homo- and copolymers of (meth)acrylates which are esterified with hydroxyalkyl(meth)acrylates.

The photopolymerisable compounds are used by themselves or in any desired mixtures. It is preferred to use mixtures of polyol(meth)acrylates.

Binders may also be added to the compositions of the invention. The addition of binders is particularly useful if the photopolymerisable compounds are liquid or viscous substances. The amount of binder may be from 5-95, preferably 10-90 and, most preferably, 40-90, percent by weight, based on the entire composition. The choice of binder will depend on the field of use and the desired properties therefor, such as the ability of the compositions to be developed in aqueous and organic solvent systems, adhesion to substrates and susceptibility to oxygen.

Suitable binders are typically polymers having a molecular weight of about 5000–2 000 000, preferably 10 000–1 000 000. Illustrative examples are: homo- and copolymers of acrylates and methacrylates, including copolymers of methyl methacrylate/ethyl acrylate/methacrylic acid, poly(alkylmethacrylates), poly(alkylacrylates); cellulose esters and ethers such as cellulose acetate, cellulose acetobutyrate, methyl cellulose, ethyl cellulose; polyvinyl butyral, polyvinyl formal, cyclised rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), polyesters such as poly(ethylene glycol terephthalate) and poly(hexamethylene glycol succinate).

The unsaturated compounds can also be used in admixture with non-photopolymerisable film-forming components. These components may be physically drying polymers or solutions thereof in organic solvents, for example nitrocellulose or cellulose acetobutyrate. They may, however, also be chemically or thermally curable resins such as polyisocynates, polyepoxides or melamine resins. The concurrent use of thermally curable resins is important for the use in so-called hybrid systems which, in a first step, are photopolymerised and, in a second step, crosslinked by a thermal aftertreatment.

In addition to the photoinitiator, the photopolymerisable compositions can contain different additives. Exemplary of such further different additives are thermal inhibitors which prevent premature polymerisation, hydroquinone, hydroquinone derivatives, p-methoxyphenol, D-naphthol or sterically hindered phenols such as 2,6-di(tert-butyl)-p-cresol. To enhance the dark storage stability it is possible to add copper compounds, including copper naphthenate, copper stearate or copper octoate, phosphorus compounds, including triphenylphosphine, tributylphosphine, triethyl phosphite, triphenyl phosphite, or tribenzyl phosphite, quaternary ammonium compounds, such as tetramethylammonium chloride or trimethylbenzylammonium chloride, or hydroxylamine derivatives, such as N-diethylhydroxylamine. The exclusion of atmospheric oxygen during the polymerisation may be effected by adding paraffin or similar wax-like substances which, at the onset of polymerisation, migrate to the surface owing to lack of solubility in the polymer and form a transparent film which prevents air from entering the system. Minor amounts of UV absorbers, typically those of the benzotriazole, benzophenone, oxanilide or hydroxyphenyl-S-triazine type, may be added as light stabilisers. Better still is the addition of light stabilisers that do not absorb UV light, for example sterically hindered amines (HALS).

The photopolymerisation can be accelerated by adding amines such as triethanolamine, N-methyl-diethanolamine, ethyl p-dimethylaminobenzoate or Michler's ketone. The action of the amines can be intensified by the addition of aromatic ketones of the benzophenone type.

The photopolymerisation can further be accelerated by the addition of photosensitisers which shift or broaden the spectral sensitivity. These photosensitisers are preferably aromatic carbonyl compounds such as benzophenone, thioxanthone, anthraquinone and 3-acylcoumarin derivatives as well as 3-(aroylmethylene)-thiazolines.

Depending on the envisaged end use further customary additives are fluorescent whitening agents, fillers, pigments, dyes, wetting agents or flow control agents. For curing thick and pigmented coatings it is convenient to add the micro-glass beads or pulverised glass fibres described, inter alia, in U.S. Pat. No. 5 013 768.

The invention also relates to compositions comprising as component (a) at least one ethylenically unsaturated photopolymerisable compound which is dissolved or emulsified in water.

Many varieties of such photocurable aqueous prepolymer dispersions are commercially available. Such dispersions will generally be understood as meaning dispersions comprising water and at least one prepolymer dispersed therein. The concentration of water in these systems is in the range from typically 5 to 80% by weight, preferably 30 to 60% by weight. The dispersions contain the photocurable prepolymer or mixture thereof in a concentration of 95 to 20% by weight, preferably of 70 to 40% by weight. The sum of the indicated percentages of water and prepolymers in these compositions is always 100. Depending on the end use, the modifiers and additives are added in varying amounts.

The photocurable film-forming prepolymers which are dispersed, and often dissolved, in water are mono- or polyfunctional, ethylenically unsaturated prepolymers which can be initiated by free radicals and are known per se for use in aqueous prepolymer dispersions. They typically contain from 0.01 to 1.0 mol of polymerisable double bonds per 100 g of prepolymer and also have an average molecular weight of at least 400, preferably of 500 to 10 000. Depending on the envisaged end use, however, prepolymers of higher molecular weight are also suitable, including polyesters having an acid number of not more than 10 and containing polymerisable C—C double bonds, polyethers containing polymerisable C—C double bonds, hydroxyl group containing reaction products of a polyepoxide containing at least two epoxy groups per molecule with at least one $\alpha,\beta$-ethylenically unsaturated carboxylic acid, polyurethane(meth)acrylates as well as the acrylic copolymers containing $\alpha,\beta$-ethylenically unsaturated acrylic radicals described in EP-A-12 339. It is also possible to use mixtures of these prepolymers. Also suitable are the polymerisable prepolymers disclosed in EP-A-33 896 which are thioether polyadducts of polymerisable prepolymers having an average molecular weight of at least 600, a carboxyl group value of 0.2 to 15%, and containing 0.01 to 0.8 mol of polymerisable C—C double bonds per 100 g of prepolymer. Other suitable aqueous dispersions based on special alkyl (meth)acrylate polymers are disclosed in EP-A-41 125. Suitable water-dispersible photocurable prepolymers of urethane acrylates are disclosed in DE-A-29 36 039.

As further additives these photocurable aqueous prepolymer dispersions may contain dispersants, emulsifiers, antioxidants, light stabilisers, dyes, pigments, fillers such as talcum, gypsum, rutile, carbon black, zinc oxide, iron oxides, reaction accelerators, flow control agents, lubricants, wetting agents, thickeners, dulling agents, antifoams and other modifiers conventionally used in coating technology. Suitable dispersants are water-soluble high molecular weight organic compounds carrying polar groups, typically polyvinyl alcohols, polyvinyl pyrrolidone or cellulose ethers. Suitable emulsifiers may be nonionic emulsifiers, if necessary, ionic emulsifiers may also be employed.

The photopolymerisable compositions contain the photoinitiator conveniently in an amount of 0.05 to 15% by weight, preferably 0.2 to 5% by weight, based on the composition.

In specific cases it is advantageous to use mixtures of two or more photoinitiators of this invention. Mixtures with known photoinitiators may of course also be used, typically mixtures with benzophenones, acetophenone derivatives, such as α-hydroxyalkylphenylketones, benzoin alkyl ethers and benzil ketals, or acyl phosphine oxides, bisacylphosphine oxides or titanocenes.

Preferred compositions are those wherein component (b) is a mixture of isomeric compounds of formula I in which p and q have different values.

The photopolymerisable compositions are used for a variety of utilities, typically as printing ink formulations, clear coating formulations, white enamel formulations for wood or metal, as coating materials for paper, wood or plastics, as UV-curable coating materials for exterior coatings and mad markings, as printing ink formulations for photographic reproduction processes, for image recording processes or for the production of printing plates which can be developed with organic solvents or aqueous alkaline media, for making masks for screen printing, as dental filling compositions, as adhesives, as discharge or permanent resists, as solder masks for electronic circuits, for making three-dimensional objects by mass hardening (UV curing in transparent formes) or by the stereolithographic method disclosed in U.S. Pat. No. 4 575 330, for fabricating composites (e.g. styrene polyesters which may contain glass fibres and other modifiers) and other thick-layered materials, for coating or sealing electronic components or as coatings for optical fibres.

In coating formulations there are frequently used mixtures of a prepolymer with polyunsaturated monomers which may contain an additional mono-unsaturated monomer. The prepolymer primarily determines the properties of the coat and, by varying it, the skilled person can influence the properties of the cured film. The polyunsaturated monomer acts as crosslinker which makes the coating film insoluble. The monounsaturated monomer acts as reactive diluent with the aid of which the viscosity is lowered without having to use a solvent.

Unsaturated polyester resins are normally used together in two-component systems with a mono-unsaturated monomer, preferably with styrene. Specific single component systems are often used for photoresists, for example the polymaleimides, polychalcones or polyimides disclosed in DE-OS 2 308 830.

The photocurable compositions of this invention may suitably be used as coating compositions for substrates of all kinds, such as wood, paper, ceramics, synthetic resins such as polyesters and cellulose acetate films, and metals such as copper and aluminium, to which it is desired to apply a protective layer or an image by photopolymerisation.

The substrate can be coated by applying to said substrate a liquid composition, a solution or suspension. This is done typically by dip-coating, brushing, spraying or reverse roller coating. The add-on (layer thickness) and the nature of the substrate (support) will depend on the desired field of application. Suitable substrates for recording photographic information are sheets of polyester, cellulose acetate or resin-coated papers. Specially treated aluminium is used for offset printing formes, and copper-clad laminates for making printed circuit boards. The layer thicknesses for photographic materials and offset printing formes are normally about 0.5 to about 10 gm. Solvents concurrently used can be removed after coating.

Photocuring is of great importance for printing inks, as the drying time of the binder is a decisive factor in the rate of production of graphic products and should be in the order of fractions of seconds. UV curable printing inks are of particular importance for screen printing.

The photocurable compositions of this invention are also very suitable for making printing plates. For this utility mixtures of soluble linear polyamides or styrene/butadiene rubber with photopolymerisable monomers, typically acrylamides, and a photoinitiator, are used. Films and plates of these systems (wet or dry) are exposed via the negative (or positive) of the original and the non-cured pans are subsequently eluted with a solvent.

A further field of use of photocuring is metal coating, as in the coating of sheet metal and tubes, cans or bottle caps, as well as the photocuring of resin coatings, for example PVC floor or wall coverings.

Illustrative of the photocuring of paper coatings is the colourless coating of labels, record sleeves or book jackets.

The use of photocurable compositions is also important for imaging techniques and for the optical production of information carders. For these utilities, the layer (wet or dry) applied to the substrate is irradiated through a photomask with shortwave light and the unexposed areas of the layer are removed by treatment with a solvent (=developer). The application of the photocurable layer can also be effected by electrodeposition on metal. The exposed areas are crosslinked-polymeric and hence insoluble and remain on the substrate. Visible images are formed by appropriate colouration. If the substrate is a metallised layer, then the metal can be etched away after exposure and development at the unexposed areas or reinforced by galvanising. In this manner it is possible to make printed circuit boards and photoresists.

Polymerisation is carried out by known methods of photopolymerisation by irradiation with sunlight or with light which is rich in shortwave radiation. Suitable light sources are typically mercury medium-pressure, high-pressure and low-pressure lamps, superactinic fluorescent tubes, metal halide lamps or lasers the maximum emissions of which are in the range from 250–450 nm. Laser light sources have the advantage that no photomasks are necessary, as the controlled laser beam writes direct onto the photocurable layer. Where combinations with photosensitisers are used, it is also possible to use light of longer wavelength or laser beams of up to 600 nm.

The invention further relates to a process for photopolymerising compounds containing ethylenically unsaturated double bonds, which comprises irradiating a composition as described above with light in the range from 200 to 600 nm.

The invention further relates to a cured composition which is obtained by the above described process.

Example 1

A) Preparation of 9-(2,6-dimethoxybenzoyl)-9-phosphabicyclo[4.2.1]nonane and 9-(2,6-dimethoxybenzoyl)-9-phosphabicyclo[3.3.1]nonane A solution of 22.1 g (0.11 mol) of 2,6-dimethoxybenzoyl chloride in 50 ml of toluene is added dropwise at 20°-30° C. over 60 min to 25.6 g (0.10 mol, 55.5% in toluene) of a mixture of 9H-phosphabicyclo[4.2.1]nonane and 9H-phosphabicyclo[3.3.1]nonane isomers (®Phoban; HOECHST) and 30.4 g (0.22 mol) of potassium carbonate in 100 ml of toluene. The reaction mixture is stirred for 2 h at the same temperature to bring the reaction to completion. The reaction mixture is washed once with water and the organic phase is separated, dried over magnesium sulfate and concentrated. The residue is recrystallised from ethyl acetate, affording 11.3 g (36.9% of theory) of the title compounds in the ratio of 1:4 as a yellowish powder with a melting point of 119°-122° C.

Elemental Analysis
calcd.: C 66.5% found: C 66.34%
H 7.57% H 7.10%

B) Preparation of 9-(2,6-dimethoxybenzoyl)-9-phosphabicyclo[4.2.1]nonane-9-sulfide and 9-(2,6-dimethoxybenzoyl)-9-phosphabicyclo[3.3.1]nonane-9-sulfide 7.7 g (0,025 mol) of a mixture of 9-(2,6-dimethoxybenzoyl)-9-phosphabicyclo[4.2.1]nonane and 9-(2,6-dimethoxybenzoyl)-9-phosphabicyclo[3.3.1]nonane isomers in 50 ml of toluene are charged to a reactor and, while introducing nitrogen, heated to 60° C., whereupon the educt dissolves completely. Then 0.8 g (0,025 mol) of sulfur are added at 60° C. and the reaction mixture is subsequently stirred for 6 h. After cooling to room temperatur, the reaction mixture is concentrated under vacuum and the residue is recrystallised from ethyl acetate, affording 6.5 g (76.7% of theory) of the title compounds in the ratio 1:6 as a yellowish powder with a melting point of 135°-140° C.

Elemental analysis:
calcd: C: 60.34% found: C: 60.17%
H: 6.85% H: 6.75%
S: 9.47% S: 9.74%

Example 2

Preparation of 9-(2,4,6-trimethylbenzoyl)-9-phosphabicyclo[4.2.1]nonanesulfide and 9-(2,4,6-trimethylbenzoyl)-9-phosphabicyclo[3.3.1]nonanesulfide A solution of 20.1 g (0.11 mol) of 2,4,6-trimethylbenzoyl chloride in 50 ml of toluene is added dropwise at 20°-30° C. over 30 min to 25.6 g (0.10 tool, 55.5% in toluene) of a mixture of 9H-phosphabicyclo[4.2.1]nonane and 9H-phosphabicyclo[3.3.1]nonane isomers (®Phoban; HOECHST) and 30.4 g (0.22 mol) of potassium carbonate in 150 ml of toluene. The reaction mixture is stirred for 10 h at the same temperature to bring the reaction to completion. The reaction mixture is washed once with water and the organic phase is separated, dried over magnesium sulfate and filtered. The yellowish solution so obtained is heated to 60° C. while introducing nitrogen and, at this temperature, 3.2 g (0.10 mol) of sulfur are added. The reaction mixture is stirred for 3 h and then cooled to room temperature, and the yellow solution is concentrated under vacuum. The mixture of isomers is purified by chromatography (eluant: hexane/diisopropyl ether 9:1) and then recrystallised from a mixture of hexane/ethyl ester to give 5.0 g (15.6% of theory) of 9-(2,4,6-trimethylbenzoyl)-9-phosphabicyclo[3.3.1]nonanesulfide (I) as a yellow powder with a melting point of 94°-95° C. and 2.8 g (8.8% of theory) of 9-(2,4,6-trimethylbenzoyl)-9-phosphabicyclo[4.2.1]nonanesulfide (II) with a melting point of 142°-144° C.

Elemental Analysis
(I) calcd.:
C: 67.47% found: C: 67.34%
H: 7.86% H: 7.91
S: 10.01% S: 10.40
(II) calcd.:
C: 67.47% found: C: 65.83%
H: 7.86% H: 8.01
S: 10.01% S: 12.61

Example 3

Reactivity in a white enamel formulation

A UV curable white enamel formulation is prepared by mixing 67.5 parts of a polyester acrylate oligomer (®Ebecryl 830, UCB, Belgium)
5.0 parts of hexanediol diacrylate
2.5 parts of trimethylolpropane triacrylate
25.0 parts of titanium dioxide (rutile type ®R-TC2, Tioxide, France)
2.0 parts of photoinitiator The formulation is applied with a 100 μm split doctor blade to a coil-coat metal sheet and then cured. The layer is cured by passing the specimen on a belt moving at a speed of 10 m/min under a 80 W/cm mercury medium-pressure lamp (Hanovia, U.S.A.). The wipe resistance (WR) is measured as the number of passes that are necessary to obtain a wipe-resistant surface. The pendulum hardness (PH) in [s]according to König (DIN 53157) is also determined. The measurement is made by first testing the wipe-resistant surface and then testing again after an additional exposure of 15 min under TL 40/03 low-pressure mercury lamps (Philips; emission maximum at 430 nm). The result is shown in Table 2.

TABLE 2

| Photoinitiator of Example | WR n × 10 m/min | PH [s] WR | PH [s] after 15 min |
|---|---|---|---|
| 1B | 5 | 126 | 142 |

What is claimed is:
1. A compound of formula I

$$R_1-\overset{O}{\underset{\|}{C}}-\overset{(S)_n}{\underset{\|}{P}} \underset{(CH_2)_p}{\diagdown} \underset{(CH_2)_q,}{\diagup}$$
(I)

wherein
n is 1,
p is a number from 1 to 8,
q is 2 or 3, and
$R_1$ is unsubstituted phenyl or phenyl which is substituted by one to three halogen, $C_1$–$C_8$alkyl, $C_1$–$C_8$alkoxy, $C_2$–$C_8$alkoxyalkyl or $C_1$–$C_4$alkylthio or mixture thereof.

2. A compound according to claim 1, wherein $R_1$ is a radical of the formula H

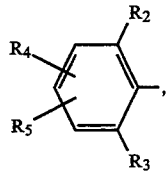
(II)

wherein $R_2$ and $R_3$ are each independently of the other halogen, $C_1$–$C_4$alkyl or $C_1$–$C_4$alkoxy, and $R_4$ and $R_5$ are each independently of the other halogen, $C_1$–$C_4$alkyl, $C_1$–$C_4$alkoxy or hydrogen.

3. A compound according to claim 2, wherein $R_4$ is $C_1$–$C_4$alkyl, $C_1$–$C_4$alkoxy or hydrogen and $R_5$ is hydrogen.

4. A compound according to claim 2, wherein $R_2$ and $R_3$ are each independently of the other $C_1$–$C_4$alkyl or $C_1$–$C_4$alkoxy, $R_4$ is hydrogen or $C_1$–$C_4$alkyl and $R_5$ is hydrogen.

5. A compound according to claim 2, wherein $R_4$ is in the para-position of the phenyl ring.

6. A compound according to 1, wherein p is 1 to 4.

7. A compound according to claim 1 which is 9-(2,6-dimethoxybenzoyl)-9-phosphabicyclo[4.2.1]nonane-9-sulfide; 9-(2,6-dimethoxybenzoyl)-9-phosphabicyclo[3.3.1]nonane-9-sulfide; 9-(2,4,6-trimethylbenzoyl)-9-phosphabicyclo[4.2.1]nonane-9-sulfide; or 9-(2,4,6-trimethylbenzoyl)-9-phosphabicyclo[3.3.1]nonane-9-sulfide.

* * * * *